US010744070B2

(12) United States Patent
Demetriades et al.

(10) Patent No.: US 10,744,070 B2
(45) Date of Patent: Aug. 18, 2020

(54) ENTERAL FAST ACCESS TRACT PLATFORM SYSTEM

(71) Applicant: University of Southern California, Los Angeles, CA (US)

(72) Inventors: Elizabeth Demetriades, Los Angeles, CA (US); Philong Pham, Los Angeles, CA (US); Behrokh Khoshnevis, Los Angeles, CA (US); Hongsheng Tong, Los Angeles, CA (US)

(*) Notice: Subject to any disclaimer, the term of this patent is extended or adjusted under 35 U.S.C. 154(b) by 140 days.

(21) Appl. No.: 15/737,212

(22) PCT Filed: Jun. 17, 2016

(86) PCT No.: PCT/US2016/038159
§ 371 (c)(1),
(2) Date: Dec. 15, 2017

(87) PCT Pub. No.: WO2016/205701
PCT Pub. Date: Dec. 22, 2016

(65) Prior Publication Data
US 2018/0200151 A1    Jul. 19, 2018

Related U.S. Application Data

(60) Provisional application No. 62/182,361, filed on Jun. 19, 2015.

(51) Int. Cl.
*A61J 15/00* (2006.01)
*A61N 1/36* (2006.01)
(Continued)

(52) U.S. Cl.
CPC ............ *A61J 15/003* (2013.01); *A61B 17/00* (2013.01); *A61C 8/0093* (2013.01); *A61F 2/04* (2013.01);
(Continued)

(58) Field of Classification Search
CPC ... A61B 17/00; A61B 17/24; A61B 2017/345; A61C 8/0093; A61F 2002/044;
(Continued)

(56) References Cited

U.S. PATENT DOCUMENTS 4,134,405 A    1/1979 Smit
4,166,452 A    9/1979 Generales, Jr.
(Continued)

FOREIGN PATENT DOCUMENTS

CA    2377502 A1    1/2001
CA    2897448 A1    7/2014
(Continued)

OTHER PUBLICATIONS

Non-Final Office Action dated Mar. 6, 2019, from U.S. Appl. No. 15/737,257.
(Continued)

*Primary Examiner* — Imani N Hayman
(74) *Attorney, Agent, or Firm* — Foley & Lardner LLP

(57) ABSTRACT

A gastrointestinal administration device comprising an elongated tube or track, an anchor and a channel, which allows the proximal end of the tube or track to be wholly secured inside the mouth from where it passes down the lateral oropharynx to the desired site in the gastrointestinal tract. This system may be used to administer nutrients, fluids, medications, nutraceuticals, dietary supplements and/or non-nutrient gastrointestinal stimulants or other therapies directly to a desired site in the gastrointestinal tract in humans and animals for a variety of purposes including novel applications such as weight and glucose control, local administration of medication and storage of a deposit of a therapeutic agent. It may also be used for monitoring of processes inside the gastrointestinal tract.

17 Claims, 9 Drawing Sheets

(51) Int. Cl.
 *A61F 2/04* (2013.01)
 *A61B 17/00* (2006.01)
 *A61N 1/00* (2006.01)
 *A61C 8/00* (2006.01)
 *A61M 25/04* (2006.01)
 *A61M 29/02* (2006.01)
 *A61B 17/24* (2006.01)
 *A61B 17/34* (2006.01)
 *A61N 1/05* (2006.01)

(52) U.S. Cl.
 CPC ............ *A61J 15/00* (2013.01); *A61J 15/0003* (2013.01); *A61J 15/0034* (2013.01); *A61M 25/04* (2013.01); *A61M 29/02* (2013.01); *A61N 1/00* (2013.01); *A61N 1/36007* (2013.01); *A61B 17/24* (2013.01); *A61B 2017/345* (2013.01); *A61F 2002/044* (2013.01); *A61N 1/0509* (2013.01)

(58) Field of Classification Search
 CPC ......... A61F 2/04; A61J 15/00; A61J 15/0003; A61J 15/003; A61J 15/0034; A61M 25/04; A61M 29/02; A61N 1/00; A61N 1/0509; A61N 1/36007
 See application file for complete search history.

(56) References Cited

U.S. PATENT DOCUMENTS

| | | |
|---|---|---|
| 4,256,108 A | 3/1981 | Theeuwes |
| 4,265,874 A | 5/1981 | Bonsen et al. |
| 4,900,306 A | 2/1990 | Quinn et al. |
| 5,026,559 A | 6/1991 | Eichel et al. |
| 5,322,697 A | 6/1994 | Meyer |
| 5,360,614 A | 11/1994 | Fox et al. |
| 5,470,839 A | 11/1995 | Laughlin et al. |
| 5,536,156 A | 7/1996 | Fox et al. |
| 5,545,410 A | 8/1996 | Fox et al. |
| 5,576,306 A | 11/1996 | Dressman et al. |
| 5,611,787 A | 3/1997 | Demeter et al. |
| 5,753,253 A | 5/1998 | Meyer |
| 5,776,887 A | 7/1998 | Wibert et al. |
| 5,811,388 A | 9/1998 | Friend et al. |
| 5,977,175 A | 11/1999 | Lin |
| 5,998,363 A | 12/1999 | Forse et al. |
| 6,103,269 A | 8/2000 | Wunderlich et al. |
| 6,143,786 A | 11/2000 | Gohman et al. |
| 6,248,375 B1 | 6/2001 | Gilles et al. |
| 6,248,390 B1 | 6/2001 | Stillman |
| 6,267,988 B1 | 7/2001 | Meyer |
| 6,420,350 B1 | 7/2002 | Fleischner |
| 6,558,690 B2 | 5/2003 | Portman |
| 6,558,708 B1 | 5/2003 | Lin |
| 6,569,463 B2 | 5/2003 | Patel et al. |
| 6,624,210 B1 | 9/2003 | Petereit et al. |
| 6,716,815 B2 | 4/2004 | Portman |
| 6,770,620 B2 | 8/2004 | Henriksen |
| 6,774,111 B1 | 8/2004 | Wolf et al. |
| 6,809,115 B2 | 10/2004 | Katz et al. |
| 6,846,891 B2 | 1/2005 | Petereit et al. |
| 7,025,791 B2 | 4/2006 | Levine et al. |
| 7,037,344 B2 | 5/2006 | Kagan et al. |
| 7,048,906 B2 | 5/2006 | Lin et al. |
| 7,081,239 B2 | 7/2006 | Lin |
| 7,122,058 B2 | 10/2006 | Levine et al. |
| 7,157,100 B2 | 1/2007 | Doshi et al. |
| 7,169,416 B2 | 1/2007 | Koss et al. |
| 7,347,875 B2 | 3/2008 | Levine et al. |
| 7,641,924 B2 | 1/2010 | Mizumoto et al. |
| 7,670,627 B2 | 3/2010 | Shefer et al. |
| 7,718,194 B2 | 5/2010 | Chenevier et al. |
| 7,766,861 B2 | 8/2010 | Levine et al. |
| 7,785,291 B2 | 8/2010 | Marco et al. |
| 7,794,447 B2 | 9/2010 | Dann et al. |
| 7,815,947 B2 | 10/2010 | Mizumoto et al. |
| 7,935,073 B2 | 5/2011 | Levine et al. |
| 8,226,602 B2 | 7/2012 | Quijana et al. |
| 8,486,153 B2 | 7/2013 | Levine et al. |
| 8,586,103 B2 | 11/2013 | Li et al. |
| 8,821,429 B2 | 9/2014 | Vargas |
| 8,828,953 B2 | 9/2014 | Baron et al. |
| 8,865,649 B2 | 10/2014 | Hageman |
| 8,882,698 B2 | 11/2014 | Levine et al. |
| 9,060,844 B2 | 6/2015 | Kagan et al. |
| 9,066,536 B2 | 6/2015 | Astrup et al. |
| 2001/0036495 A1 | 11/2001 | Ganan-Calvo |
| 2003/0130346 A1 | 7/2003 | Kuzela et al. |
| 2003/0192552 A1 | 10/2003 | Mongeon |
| 2003/0220413 A1 | 11/2003 | Petereit et al. |
| 2004/0018190 A1 | 1/2004 | Ando et al. |
| 2004/0132819 A1 | 7/2004 | Auestad et al. |
| 2004/0197380 A1 | 10/2004 | Wolf et al. |
| 2004/0234631 A1 | 11/2004 | Hoie |
| 2005/0014345 A1 | 1/2005 | Miyamoto et al. |
| 2005/0038415 A1 | 2/2005 | Rohr et al. |
| 2005/0143459 A1 | 6/2005 | Kuzela et al. |
| 2005/0154064 A1 | 7/2005 | Piomelli et al. |
| 2005/0175763 A1 | 8/2005 | Purpura et al. |
| 2006/0046969 A1 | 3/2006 | Maggio |
| 2006/0141103 A1 | 6/2006 | Heritage et al. |
| 2006/0178560 A1 | 8/2006 | Saadat et al. |
| 2006/0204576 A1 | 9/2006 | Petereit et al. |
| 2007/0198074 A1 | 8/2007 | Dann et al. |
| 2008/0020041 A1 | 1/2008 | Ayres |
| 2009/0011019 A1 | 1/2009 | Jahagirdar et al. |
| 2009/0093767 A1 | 4/2009 | Kelleher |
| 2009/0093839 A1 | 4/2009 | Kelleher |
| 2009/0181109 A1 | 7/2009 | Barker |
| 2009/0252767 A1 | 10/2009 | Durig et al. |
| 2010/0016425 A1 | 1/2010 | Vath |
| 2010/0056948 A1 | 3/2010 | Hornby et al. |
| 2010/0203134 A1 | 8/2010 | Chenevier et al. |
| 2010/0267643 A1 | 10/2010 | Baron et al. |
| 2011/0065660 A1 | 3/2011 | Baron et al. |
| 2011/0076326 A1 | 3/2011 | Caillard et al. |
| 2011/0081400 A1 | 4/2011 | Langford et al. |
| 2011/0117192 A1 | 5/2011 | Navon et al. |
| 2011/0178005 A1 | 7/2011 | Yamka et al. |
| 2011/0217380 A1 | 9/2011 | Geraedts et al. |
| 2011/0268666 A1 | 11/2011 | Friedman et al. |
| 2011/0268795 A1 | 11/2011 | Fayad |
| 2012/0052151 A1 | 3/2012 | Sannino et al. |
| 2012/0064143 A1 | 3/2012 | Sharp et al. |
| 2012/0094942 A1 | 4/2012 | Baron et al. |
| 2013/0035559 A1 | 2/2013 | Hornby et al. |
| 2013/0150823 A1 | 6/2013 | Montgomery et al. |
| 2013/0273154 A1 | 10/2013 | Fayad et al. |
| 2013/0337055 A1 | 12/2013 | Schentag et al. |
| 2014/0127299 A1 | 5/2014 | Dordunoo |
| 2014/0127307 A1 | 5/2014 | Venkatesh et al. |
| 2014/0127351 A1 | 5/2014 | Disilvestro |
| 2014/0141082 A1 | 5/2014 | Gao |
| 2014/0193498 A1 | 7/2014 | Baron et al. |
| 2014/0194805 A1 | 7/2014 | Levine et al. |
| 2014/0294951 A1 | 10/2014 | Fayad et al. |
| 2014/0377353 A1 | 12/2014 | Borges De Brito |
| 2015/0038453 A1 | 2/2015 | Hageman |
| 2015/0038583 A9 | 2/2015 | Kabaradjian |
| 2015/0118298 A1 | 4/2015 | Zhang et al. |
| 2015/0150894 A1 | 6/2015 | Baron et al. |
| 2015/0173405 A1 | 6/2015 | Van Der Beek et al. |
| 2015/0230510 A1 | 8/2015 | Navia et al. |
| 2015/0306128 A1 | 10/2015 | Armstrong |
| 2015/0320817 A1 | 11/2015 | Astrup et al. |
| 2018/0168216 A1 | 6/2018 | Demetriades et al. |

FOREIGN PATENT DOCUMENTS

| | | |
|---|---|---|
| CA | 2899220 A1 | 8/2014 |
| CN | 1555729 A | 12/2004 |
| CN | 101125132 A | 2/2008 |
| CN | 101223987 A | 7/2008 |

(56) References Cited

FOREIGN PATENT DOCUMENTS

| | | |
|---|---|---|
| CN | 102935106 A | 2/2013 |
| CN | 103211148 A | 7/2013 |
| CN | 103284275 A | 9/2013 |
| CN | 103300374 A | 9/2013 |
| CN | 103385469 A | 11/2013 |
| CN | 103416801 A | 12/2013 |
| CN | 103584083 A | 2/2014 |
| CN | 103652862 A | 3/2014 |
| CN | 103719756 A | 4/2014 |
| CN | 103750338 A | 4/2014 |
| CN | 103766870 A | 5/2014 |
| CN | 104107188 A | 10/2014 |
| CN | 103478792 B | 12/2014 |
| CN | 104187670 A | 12/2014 |
| CN | 104286849 A | 1/2015 |
| CN | 104305206 A | 1/2015 |
| CN | 104623097 A | 5/2015 |
| CN | 104856059 A | 8/2015 |
| EP | 0 724 842 A2 | 8/1996 |
| EP | 0 898 900 A2 | 3/1999 |
| EP | 1 129 711 A2 | 9/2001 |
| EP | 1 371 368 A1 | 12/2003 |
| EP | 1 143 988 B1 | 2/2004 |
| EP | 1 513 541 B1 | 1/2009 |
| EP | 2 085 089 A1 | 8/2009 |
| WO | WO-2011/059672 A2 | 5/2011 |
| WO | WO-2012/055577 A1 | 5/2012 |
| WO | WO-2014/134225 A2 | 9/2014 |
| WO | WO-2014/197632 A2 | 12/2014 |
| WO | WO-2014/204382 A1 | 12/2014 |
| WO | WO-2015/063038 A1 | 5/2015 |
| WO | WO-2015/085010 A1 | 6/2015 |
| WO | WO-2015/086467 A1 | 6/2015 |
| WO | WO-2015/120471 A1 | 8/2015 |
| WO | WO-2015/140798 A2 | 9/2015 |
| WO | WO-2016/205701 A1 | 12/2016 |
| WO | WO-2016/205754 A1 | 12/2016 |

OTHER PUBLICATIONS

Non-Final Office Action dated May 29, 2019, from U.S. Appl. No. 13/918,808.

U.S. Restriction Office Action dated Nov. 20, 2018, from U.S. Appl. No. 15/737,257.

Ackerman M H et al. (2006), "Technologic approaches to determining proper placement of enteral feeding tubes", AACN Adv Crit Care, 17(3):246-249.

American Diabetes Association (2013), "Economic costs of diabetes in the U.S. in 2012", Diabetes Care, 36(4): 1033-1046.

Aron-Wisnewsky J et al. (2012), "The importance of the gut microbiota after bariatric surgery", Nat Rev Gastroenterol Hepatol., 9(10): 590-598.

Ashrafian H et al. (2011), "Diabetes resolution and hyperinsulinaemia after metabolic Roux-en-Y gastric bypass", obesity reviews, 12(5): e257-e272.

Aspire Bariatrics—AspireAssist Non-Surgical Weight Loss, http://www.aspirebariatrics.com/, retrieved on Aug. 10, 2016.

Beckman L M etal. (2011), "Changes in gastrointestinal hormones and leptin after Roux-en-Y gastric bypass surgery", JEPN J Parenter Enteral Nutr., 35(2):169-180.

Beglinger S et al. (2010), "Role of fat hydrolysis in regulating glucagon-like Peptide-1 secretion", J Clin Endocrinol Metab., 95(2): 879-886.

Bosi E (2010), "Time for testing incretin therapies in early type 1 diabetes?", J Clin Endocrinol Metab., 95(6): 2607-2609.

Bradley D et al. (2012), "Effects of bariatric surgery on glucose homeostasis and type 2 diabetes", Gastroenterology, 143(4):897-912.

Bray G A (2016), "Obesity in adults: Health hazards", In: UpToDate, Martin KA (Dep Ed), UpToDate, Waltham, MA (Accessed on Aug. 12, 2016).

Buchwald H et al. (2004), "Bariatric surgery: a systematic review and meta-analysis", JAMA, 292(14): 1724-1737.

Chaikomin R et al. (2008), "Effects of mid-jejunal compared to duodenal glucose infusion on peptide hormone release and appetite in healthy men", Regul Pept., 150(1-3): 38-42.

ClinicalTrials.gov, "Levodopa-Carbidopa Intestinal Gel Open-Label Study in Advanced Parkinson's Disease", Retrieved from http://clinicaltrials.gov/ct2/sho/NCT00335153 in Aug. 2016.

ClinicalTrials.gov, "The Role of the Duodenum in the Pathogenesis of Insulin Resistance and Type 2 Diabetes Mellitus", Retrieved from http://clinicaltrials.gov/ct2/show/NCT00568620?term=enteraltube&rank=52 on Aug. 10, 2016.

Colditz G A et al. (1995), "Weight gain as a risk factor for clinical diabetes mellitus in women", Ann Intern Med., 122(7):481-486.

Cook Medical, https://www.cookmedical.com/products/cc_njft_webds/, Retrieved in Aug. 2016.

Cortrak Enteral Access System, http://www.corpakmedsystems.com/cortrak-product-page/cortrak/, Retrieved on Aug. 11, 2016.

Czupryniak L et al. (2010), "Long-term results of gastric bypass surgery in morbidly obese type 1 diabetes patients", Obes Surg., 20(4): 506-508.

De Jonge C et al. (2011), "Endobarrier (TM) Gastrointestinal Liner Treatment Rapidly Improves Diabetes Parameters Paralleled by Increased Postprandial GLP-1 and PYY Levels in Obese Type 2 Diabetic Patients", Poster 83 Poster Sessions and Abstract Book 2nd World Congress on Interventional Therapies for Type 2 Diabetes Poster Presentation in Conference Proceedings, New York Mar. 2011.

Deane A M et al. (2009), "Evaluation of a bedside technique for postpyloric placement of feeding catheters", Crit Care Resusc., 11(3):180-183.

Dirksen C et al. (2010), "Postprandial diabetic glucose tolerance is normalized by gastric bypass feeding as opposed to gastric feeding and is associated with exaggerated GLP-1 secretion: a case report", Diabetes Care, 33(2): 375-377.

DuoDopa, https://www.duopa.com, Retrieved in Aug. 2016.

Elcelyx Pipeline, Retrieved from http://elcelyx.com/clinical/metformin-dr/ on Aug. 11, 2016.

Elcelyx Therapeutics (2012), "Elcelyx Lovidia ingredient promotes satiety", Retrieved from http://newhope.com/specialty/elcelyx-lovidia-ingredient-promotes-satiety on Aug. 11, 2016.

EndoBarrier Overview, http://www.gidynamics.com/endobarrier-overview.php, retrieved on Aug. 10, 2016.

EndoSphere, http://www.endosphereinc.com/, retrieved on Aug. 10, 2016.

Falken Y et al. (2011), "Changes in glucose homeostasis after Roux-en-Y gastric bypass surgery for obesity at day three, two months, and one year after surgery: role of gut peptides", J Clin Endocrinol Metab., 96(7):2227-2235.

Flegal K M et al. (2012), "Prevalence of obesity and trends in the distribution of body mass index among US adults, 1999-2010", JAMA, 307(5):491-497.

FoodBev Media, "Alain Baron on weight management and satiety", Posted by Shaun Weston on Nov. 5, 2012, Retrieved from http://www.foodbev.com/news/alain-baron-on-weight-management-and-sat/ on Aug. 11, 2016.

Foster-Schubert K E et al. (2008), "Acyl and total ghrelin are suppressed strongly by ingested proteins, weakly by lipids, and biphasically by carbohydrates", J Clin Endocrinol Metab., 93(5):1971-1979.

Galera S C et al. (2010), "The safety of oral use of L-glutamine in middle-aged and elderly individuals", Nutrition, 26(4):375-381.

Gaylinn B D et al. (2010), "Luminal influences to orchestrate gastroenterological hormone secretion: the fat, long-chain Fatty Acid, cholecystokinin, glucagon-like Peptide 1 axis", J Clin Endocrinol Metab., 95(2):503-504.

Geraedts M C et al. (2011), "Intraduodenal administration of intact pea protein effectively reduces food intake in both lean and obese male subjects", PLoS One. 2011, 6(9):e24878.

Gray R et al. (2007), "Bedside electromagnetic-guided feeding tube placement: an improvement over traditional placement technique?", Nutr Clin Pract., 22(4):436-444.

(56) References Cited

OTHER PUBLICATIONS

Greenfield J R et al. (2009), "Oral glutamine increases circulating glucagon-like peptide 1, glucagon, and insulin concentrations in lean, obese, and type 2 diabetic subjects", Am J Clin Nutr., 89(1):106-113.

Hall K D et al. (2011), "Quantification of the effect of energy imbalance on bodyweight", Lancet, 378(9793): 826-837.

Hansen E N et al. (2011), "Role of the foregut in the early improvement in glucose tolerance and insulin sensitivity following Roux-en-Y gastric bypass surgery", Am J Physiol Gastrointest Liver Physiol., 300(5): G795-802.

Hansen K B et al. (2011), "2-Oleoyl glycerol is a GPR119 agonist and signals GLP-1 release in humans", J Clin Endocrinol Metab., 96(9): E1409-17.

Holzinger U et al. (2011), "Jejunal tube placement in critically ill patients: A prospective, randomized trial comparing the endoscopic technique with the electromagnetically visualized method", Crit Care Med., 39(1):73-77.

International Search Report and Written Opinion dated Oct. 28, 2016, from application No. PCT/US2016/038244.

International Search Report and Written Opinion dated Sep. 7, 2016, from application No. PCT/US2016/038159.

Jacobsen S H et al. (2012), "Changes in gastrointestinal hormone responses, insulin sensitivity, and beta-cell function within 2 weeks after gastric bypass in non-diabetic subjects", Obes Surg., 22(7):1084-1096.

Kaushik, N. et al. (2005) "Enteral Feeding Without Pancreatic Stimulation," Pancreas 31(4):353-359.

Kielgast U et al. (2011), "Antidiabetic Actions of Endogenous and Exogenous GLP-1 in Type 1 Diabetic Patients With and Without Residual Beta-Cell Function", Diabetes, vol. 60, pp. 1599-1607.

Kless S et al. (2009), "Has the introduction of an electromagnetic tube placement system reduced Inappropriate parenteral nutrition utilization and associated costs?" Poster, Nutr Clin Pract. 2009, 24(1): Abstract 91.

Koopmann M C et al. (2011), "A team-based protocol and electromagnetic technology eliminate feeding tube placement complications", Ann Surg., 253(2):297-302.

Laferrere B et al. (2008), "Effect of Weight Loss by Gastric Bypass Surgery Versus Hypocaloric Diet on Glucose and Incretin Levels in Patients with Type 2 Diabetes", J Clin Endocrinol Metab, 93(7): 2479-2485.

Layer P et al. (1995), "Ileal release of glucagon-like peptide-1 (GLP-1): Association with inhibition of gastric acid secretion in humans", Dig Dis Sci., 40(5): 1074-1082.

Maahs DM et al. (2010), "Epidemiology of type 1 diabetes", Endocrinol Metab Clin North Am. 2010, 39(3):481-497.

Mackay P et al. (2009), "Corpak with Cortrak" Poster, Presented at Saint Joseph Health System; Jan. 2009; Lexington, KY.

Martins et al. (2009), "Glucose Tolerance in the Proximal Versus the Distal Small Bowel in Wistar Rats", Obes Surg., 19:202-206.

MedGadget (2013), "A Sleeve for Your Small Intestine: Interview with GI Dynamics Founder, Andy Levine", Retrieved from http://www.medgadget.com/2013/04/a-sleeve-for-your-small-intestine-interview-with-gi-dynamics-founder-andy-levine.html on Aug. 16, 2016.

Mendez C E et al. (2010), "Outcomes of Roux-en-Y gastric bypass surgery for severely obese patients with type 1 diabetes: a case series report", Diabetes Metab Syndr Obes., 3:281-283.

Mingrone G et al. (2012), "Bariatric Surgery versus Conventional Medical Therapy for Type 2 Diabetes", N Engl J Med 2012, 366(17):1577-1585.

Muscle Milk 100 Calorie Protein Shake, Retrieved from http://www.cytosport.com/products/muscle-milk/muscle-milk-light-100-calorie-ready-to-drink on Aug. 10, 2016.

Nakatani H et al. (2009), "Serum bile acid along with plasma incretins and serum high-molecular weight adiponectin levels are increased after bariatric surgery", Metabolism, 58(10): 1400-1407.

NIH Conference (1991), "Gastrointestinal surgery for severe obesity. Consensus Development Conference Panel", Ann Intern Med., 115(12):956-961.

Olivan B et al. (2009), "Effect of weight loss by diet or gastric bypass surgery on peptide YY3-36 levels", Ann Surg., 249(6):948-953.

Paniagua J A et al. (2007), "A MUFA-rich diet improves pospandial glucose, lipid and GLP-1 responses in insulin-resistant subjects", J Am Coll Nutr., 26(5):434-444.

Phang J et al. (2006), "Feeding tube placement with the aid of a new electromagnetic transmitter", JPEN J Parenter Enteral Nutr. 2006, 30(2): Abstract S082.

Pournaras D J et al. (2009), "Obesity, gut hormones, and bariatric surgery", World J Surg., 33(10): 1983-1988.

Pournaras D J et al. (2010), "Remission of Type 2 Diabetes after Gastric Bypass and Banding: Mechanisms and 2 Year Outcomes", Annals of Surgery. 2010, 252(6):966-971.

Rothstein R I (2011), "Medical Device Therapy for Obesity and Metabolic Disease—The Current Landscape", Retrieved from http://www.obesitydevices.org/DDOMD%20Session%201/Rothstein1.pdf on Aug. 10, 2016.

Rubino F et al. (2010), "Metabolic Surgery to Treat Type 2 Diabetes: Clinical Outcomes and Mechanisms of Action", Annu Rev Med 2010, 61:393-411.

Samocha-Bonet D et al. (2011), "Glutamine reduces postprandial glycemia and augments the glucagon-like peptide-1 response in type 2 diabetes patients", J Nutr., 141(7):1233-1238.

Schauer P R et al. (2012), "Bariatric Surgery versus Intensive Medical Therapy in Obese Patients with Diabetes", N Engl J Med., 366(17): 1567-1576.

Schouten R et al. (2010), "A multicenter, randomized efficacy study of the EndoBarrier Gastrointestinal Liner for presurgical weight loss prior to bariatric surgery", Ann Surg., 251(2):236-243.

Small C J et al. (2004), "Gut hormones as peripheral anti obesity targets", Abstract, Curr Drug Targets CNS Neurol Disord., 3(5):379-388.

Stefater M A et al. (2012), "All bariatric surgeries are not created equal: insights from mechanistic comparisons", Endocr Rev., 33(4): 595-622.

Stockdale W et al. (2007), "Nasoenteric feeding tube insertion utilizing an electromagnetic tube placement system" Poster, Nutr Clin Pract. 2007, 22:118.

Suarez-Pinzon W L et al. (2011), "Combination therapy with a dipeptidyl peptidase-4 inhibitor and a proton pump inhibitor induces Beta-cell neogenesis from adult human pancreatic duct cells implanted in immunodeficient mice", Cell Transplant, 20(9): 1343-1349.

Sumithran P et al. (2011), "Long-Term Persistence of Hormonal Adaptations to Weight Loss", N Engl J Med 2011, 365(17): 1597-1604.

Taylor S J et al. (2010), "Treating delayed gastric emptying in critical illness: metoclopramide, erythromycin, and bedside (cortrak) nasointestinal tube placement", JPEN J Parenter Enteral Nutr., 34(3):289-294.

Trottier S et al. (2011), "Electromagnetic guided feeding tube insertion: Enhancing patient safety", Poster presentation at: 40th Society of Critical Care Medicine Conference; Jan. 15-19, 2011; San Diego, CA; Abstract 264.

U.S. Final Office Action dated Mar. 13, 2017 in U.S. Appl. No. 13/918,808.

U.S. Final Office Action dated Mar. 21, 2018, from U.S. Appl. No. 13/918,808.

U.S. Non-Final Office Action dated Aug. 21, 2017 in U.S. Appl. No. 13/918,808.

U.S. Non-Final Office Action dated Nov. 9, 2016, from U.S. Appl. No. 13/918,808.

ValenTx—Technology, http://www.valentx.com/technology.php, retrieved on Aug. 10, 2016.

Vantyghem M C et al. (2011), "Diabetes cell therapy: a decade later", Minerva Endocrinol., 36(1): 23-39.

Ward E et al. (2003), "Oral glutamine in paediatric oncology patients: a dose finding study", Eur J Clin Nutr., 57(1):31-36.

(56) References Cited

OTHER PUBLICATIONS

Weiner J P et al. (2013), "Impact of Bariatric Surgery on Health Care Costs of Obese Persons: A 6-Year Follow-up of Surgical and Comparison Cohorts Using Health Plan Data", JAMA Surg., 148(6): 555-562.
Welch, I.M. et al. (1988) "Comparisons of the effects on satiety and eating behavior of infusion of lipid into the different regions of the small intestine," Gut 29:306-311.
Willett W C et al. (1999), "Guidelines for healthy weight", N Engl J Med., 341(6):427-434.
Notice of Allowance on U.S. Appl. No. 15/737,257 dated Oct. 30, 2019.
Final Office Action dated Oct. 22, 2019, from U.S. Appl. No. 13/918,808.
Czamocka, et al., "Gastro-Resistant Characteristics of GRAS-Grade Enteric Coatings for Pharmaceutical and Nutraceutical products", International Journal of Pharmaceutics, 486(1-2), Mar. 2015.
Final Office Action dated Aug. 21, 2019, from U.S. Appl. No. 15/737,257.

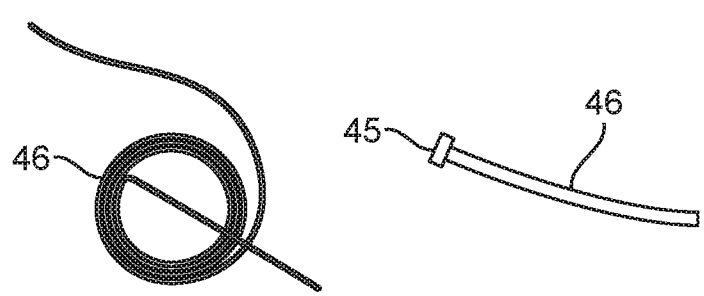
FIG. 5A
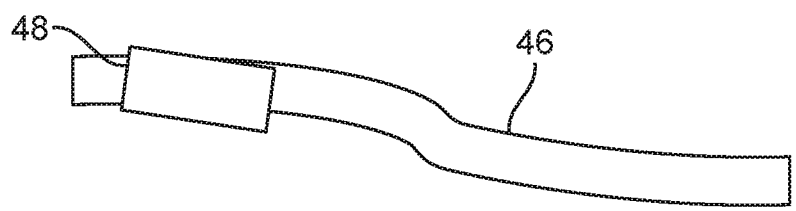
FIG. 5B
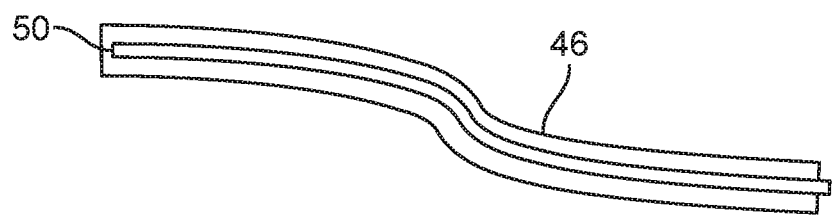
FIG. 5C
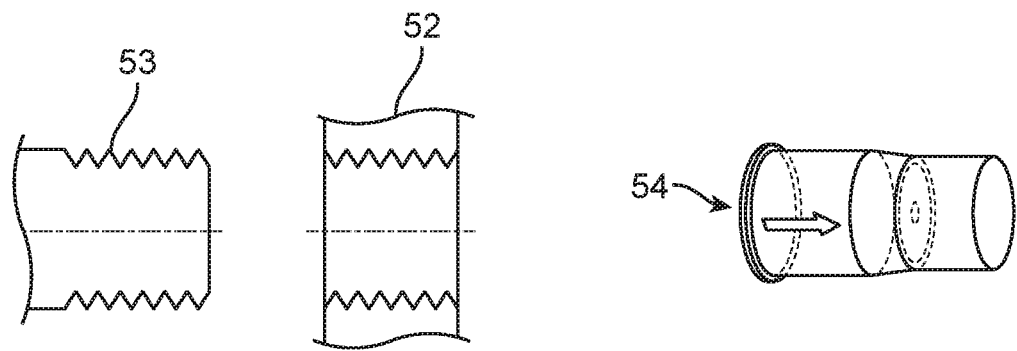
FIG. 5D
FIG. 5E

ENTERAL FAST ACCESS TRACT PLATFORM SYSTEM

CROSS-REFERENCE TO RELATED APPLICATION

This application is a national stage application under 35 U.S.C. § 371 of International Application No. PCT/US2016/038159, filed Jun. 17, 2016, which claims the benefit under 35 U.S.C. § 119(e) of U.S. Provisional Application Ser. No. 62/182,361, filed Jun. 19, 2015, the contents each of which are incorporated by reference into the present disclosure in their entireties.

BACKGROUND

The gastrointestinal tract is essentially a long tube that propels substances from one end to the other with absorption of substances along the way. In certain situations it may be desirable to modify this feature of the gastrointestinal tract to maintain a substance at or deliver a substance to a specific location for controlled release there or to maintain a device at a specific location for monitoring of internal processes.

Enteral feeding tubes are used by people of all ages and animals to deliver nutrients, fluids, medications, nutraceuticals and/or dietary supplements directly to a desired site, usually in the gastrointestinal tract, in a variety of individuals including those with difficulty swallowing (dysphagia), musculoskeletal or neurological illness, general debilitation and weakness, mental impairment and mechanical obstruction in part of the gastrointestinal tract. They can be used to maintain health or restore it.

Currently, enteral feeding tubes are designed to be secured on the body's external surface and to have some of the tube visible externally. The proximal end of a nasoenteral and oroenteral tube remains outside the nose or mouth and is usually taped to the skin or secured in place with a bridle. Such tubes can be dislodged fairly easily, are often uncomfortable and are considered unsightly by many individuals. Nasoenteral tubes can cause nasal mucosal irritation and sinusitis. They can be difficult to secure in place.

Percutaneous enteral feeding tubes are placed through a surgical procedure and pass through the skin and subcutaneous tissue and into the gastrointestinal tract, usually the stomach or upper intestine.

SUMMARY

Apparatus and methods are provided for a minimally invasive gastrointestinal administration platform. In accordance with one aspect of the present disclosure, a gastrointestinal administration device and method of use is provided, the gastrointestinal administration device comprising an elongated tube ("conduit") having an upstream end disposed in a mouth of an individual, a downstream end disposed in a gastrointestinal tract site of the individual, a wall defining a lumen, the lumen extending therethrough the upstream end and the downstream end, an access port in fluid communication with the upstream end, and at least one distribution port in fluid communication with the downstream end; a sealing mechanism for sealing the access port; an anchor disposed in the mouth, the anchor configured to secure the upstream end of the elongated conduit to at least one feature in the mouth; and a channel coupled to the anchor and is configured to receive the upstream end of the elongated conduit, wherein the elongated conduit is translatable through the channel; and wherein the access port is disposed outside of the channel and is not translatable through the channel.

In some embodiments, the feature in the mouth that the anchor secures to may include a tooth, a bone, or a cartilage, mucosa or muscle in the mouth. In some other embodiments, the feature in the mouth includes a dental prosthesis, an orthodontic appliance, a tooth included in a set of dentures, a dental crown, a molar, a premolar, a maxilla or a mandible.

In some embodiments, the anchor may be an intraoral hardware, dental prosthesis, or an orthodontic appliance. In some embodiments, the anchor may be a dental implant disposed in a tooth socket. In some other embodiments, the anchor comprises at least one of a molar band, a dental plate, dental implant, a temporary anchoring device (TAD), a denture, dental braces, Invisalign®, a dental bracket, or a dental retainer. In yet some other embodiments, the anchor comprises a strip made of biocompatible material coupled to at least one tooth. The anchor may be an artificial or synthetic device mounted to an oral feature. In some embodiments, the artificial or synthetic device is removably coupled to at least one tooth.

In some embodiments, the channel may be formed of a deformable material and may include a longitudinal recess along an entire length of an inner surface of the channel for slidably receiving the elongated conduit. In some embodiments, the channel comprises a plurality of rings in substantially coaxial alignment. In some other embodiments, the channel comprises a cylindrical tube having a channel lumen extending therethrough. In yet some other embodiments, the channel comprises two hingedly connected semi-cylindrical parts having an opened position and a closed position, and wherein the elongated conduit configured to be placed inside of the two hingedly connected semi-cylindrical parts configured to receive in the opened position. In some embodiments, the channel is configured to be coupled to the anchor via an adjustable connector, the adjustable connector having a first end and a second end, wherein the lever is configured to be attached to the anchor at the first end, and to the channel at the second end. The lever or adjustable connector may be rotatably attached to the anchor and/or the channel.

In some embodiments, the channel may be disposed at the buccal or lingual aspect of a tooth.

In some embodiments, the sealing mechanism is a cap or a one-way valve. In some embodiments, the cap is further removably engageable to the channel.

In some embodiments, the gastrointestinal administration device further includes an administration conduit having a proximal end and a distal end, the administration conduit in fluidic communication with a delivery port at the distal end and a first reservoir including a payload at the proximal end, wherein the delivery port is removably engageable to the access port of the elongated conduit; and wherein upon an engagement of the delivery port to the access port, a pressure at the first reservoir provides the payload through the at least one distribution port and into the gastrointestinal tract.

In some embodiments, the administration conduit comprises a plurality of conduit branches, each of the plurality of conduit branches having a proximal end and a distal end, and wherein each of the conduit branches is in fluid communication with a corresponding reservoir at the proximal end and the delivery port at the distal end; and wherein each corresponding reservoir comprises a corresponding payload.

In some embodiments, the delivery port may comprise a fastening feature for engaging a complementary fastening feature of the access port. One of the fastening feature and the complementary fastening feature includes a male thread and the other of the fastening feature and the complementary fastening feature comprises a female thread. In another embodiment, one of the fastening feature and the complementary fastening feature includes a funnel and the other of the fastening feature and the complementary fastening feature includes a cone. In some embodiments, the access port may include a one way valve.

In some embodiments, at least one sensor is disposed at the downstream end of the elongated conduit, the at least one sensor configured to sense at least one of pH and blood at the gastrointestinal tract site. The sensor may comprise an occult blood detecting device. In some other embodiments, an expandable distal reservoir is disposed at the downstream end of the elongated conduit, and is configured to contain and release substances in a controlled manner.

In some embodiments, the elongated conduit is retrievable and replaceable, and may comprise an upper segment and a lower segment, the lower segment is formed of a biodegradable material absorbable in a gastrointestinal tract. In some embodiments, the elongated conduit further comprises a decoupler configured to selectively engage the upper segment and the lower segment.

In some embodiments, the elongated conduit can be reinforced to prevent damage by biting. In some embodiments, the elongated conduit may further include a shape retaining material extending on or in at least a portion of the tube wall. The shape retaining material may be a shape memory alloy.

This platform device is useful to administer nutrients, fluids, medications, nutraceuticals, dietary supplements and/or non-nutrient gastrointestinal stimulants or inhibitors directly to a desired site in the gastrointestinal tract in humans and animals for immediate or later use.

This platform device may further be used to deliver agents such as prebiotics, probiotics, bile acids, microbes, and hydrogels.

This platform device may also be used to manage excess weight or for glucose control in humans and animals.

This platform device may also be used to prevent interaction of certain nutrients with specific areas of the gastrointestinal tract. For example, interaction of nutrients with the stomach and/or the upper intestine may be excluded to stimulate certain desirable aspects of gastric bypass surgery used in the management of obesity and Type 2 diabetes, and related co-morbidities. The rationale for such use is disclosed in U.S. Provisional Patent Application No. 62/182,366, filed Jun. 19, 2015, incorporated by reference herein in its entirety.

This platform device can also be used to manage other chronic diseases such as Parkinson's Disease, as erratic gastric emptying may be avoided by direct delivery of therapy to the upper intestine. Similarly, this platform system may also be used for desired activation or inhibition of enteroendocrine cells and neurohormonal pathways by nutrients or other agents.

This platform device can also be used for filling (inflating) and draining (deflating) an intragastric or intraintestinal balloon disposed in the vicinity of a selected gastrointestinal tract site.

This platform device can also be used for drainage or venting purposes, e.g., to allow intermittent release of secretions, gas, or gastric acid through the proximal end of the tube into a receptacle in individuals with gastrointestinal tract obstruction. In another embodiment, this platform device can be used for drainage of nutrients if controlled removal (e.g., with assistance of a pump) of nutrients is medically indicated, for example, for purpose of weight control.

The tube may be placed in ways that are currently standard practice. These include blind placement where the tube is inserted without visualization of its progress, endoscopically, under fluoroscopy, under electromagnetic guidance such as used in the CORPAK Medsystems, CORTRAK Enteral System, and/or with x-ray confirmation of position or other means such as auscultation for air in the stomach or check of pH in tube aspirate.

In accordance with another aspect of the present disclosure, apparatus and methods are provided for a gastrointestinal administration device comprising an elongated track having an upstream end disposed in a mouth of an individual, a downstream end disposed in a gastrointestinal tract site of the individual, and a coupler disposed at the upstream end of the elongated track, the elongated track configured to deliver a substance or a device to a selected site of the gastrointestinal tract; an anchor disposed in the mouth, the anchor configured to secure the upstream end of the elongated track to at least one feature in the mouth; and a channel coupled to the anchor and is configured to receive the upstream end of the elongated track, wherein the coupler is coupled to the channel.

In some embodiments, the elongated track is retrievable and replaceable. The elongated track may include an upper segment and a lower segment, the lower segment is formed of a biodegradable material absorbable in a gastrointestinal tract. In some embodiment, the elongated track includes a decoupler for selectively engaging the upper segment and the lower segment. In some embodiments, the elongated track is reinforced to prevent damage by biting.

In some embodiments, a stimulation device is delivered using the gastrointestinal administration device that is configured to provide one or more stimulus to the gastrointestinal tract, the stimulus comprising electrical, chemical, or mechanical stimulus. The stimulation device can be an inflatable balloon, at least one electrode, radiofrequency ablation device, or ultrasonic device.

In some embodiments, the substance to be delivered using the gastrointestinal administration device is in solid form, liquid form, or semi-liquid form. In some embodiments, the substance is configured to be delivered in dosage depots having at least one depot distribution port, which may be selectively permeable. The dosage pods are slidably or threadably coupled to the elongated track.

In some embodiments, the elongated track includes a bumper disposed at the downstream end of the track, wherein the bumper is configured to selectively obstruct the substance or device from moving further downstream relative to the elongated track.

In some embodiments, the coupler comprises a hook, a clasp, or a bump, or a thickening of the track.

The embodiments in accordance with the present disclosure have been evaluates by the inventors in human study participants and have been demonstrated to function safely, effectively, comfortably and esthetically.

BRIEF DESCRIPTION OF THE DRAWINGS

FIGS. 5A-5E illustrate exemplary embodiments of tubes and access ports.

DETAILED DESCRIPTION

Definitions

The singular form of "a", "an" and "the" include plural references unless the context clearly dictates otherwise. For example, the term "a nutrient" may include a plurality of nutrients, including mixtures thereof.

Numerical designations and numerical ranges, for example tube diameter, pH, temperature, time, concentration, and molecular weight, are approximations which are varied (+) or (−) by increments of 0.1. It is to be understood, although not always explicitly stated, that all numerical designations are preceded by the term "about". It also is to be understood, although not always explicitly stated, that the reagents described herein are merely exemplary and that equivalents of such are known in the art.

The term "comprising" intends that formulations, physical compositions and methods include the recited elements, but do not exclude others. "Consisting essentially of", when used to define systems and methods, shall mean excluding other elements of any essential significance to the combination such as those that do not contribute to the benefit of the claimed embodiments. "Consisting of" shall mean excluding more than trace elements. Embodiments defined by each of these transition terms are within the scope of this invention.

The term "individual" intends an animal, whether human or non-human. For example, an individual may be human, bovine, horse, feline, canine, rodent, or primate.

The term "gastrointestinal administration" intends the administration of a substance, a device, and/or a stimulus to the gastrointestinal tract of an individual.

As used herein, the term "anchor" intends an artificial object coupled to a feature in the mouth, thereby allowing other objects to be secured to the feature in the mouth by coupling to the anchor. The coupling of the anchor to the feature in the mouth may be permanent or removable. Similarly, the coupling of the anchor to the other objects may be permanent or removable.

As used herein, a "reservoir" intends a device for containing a payload such as a substance. The substance may be solid, semi-solid, or liquid.

Summary of Components

Figure 1:
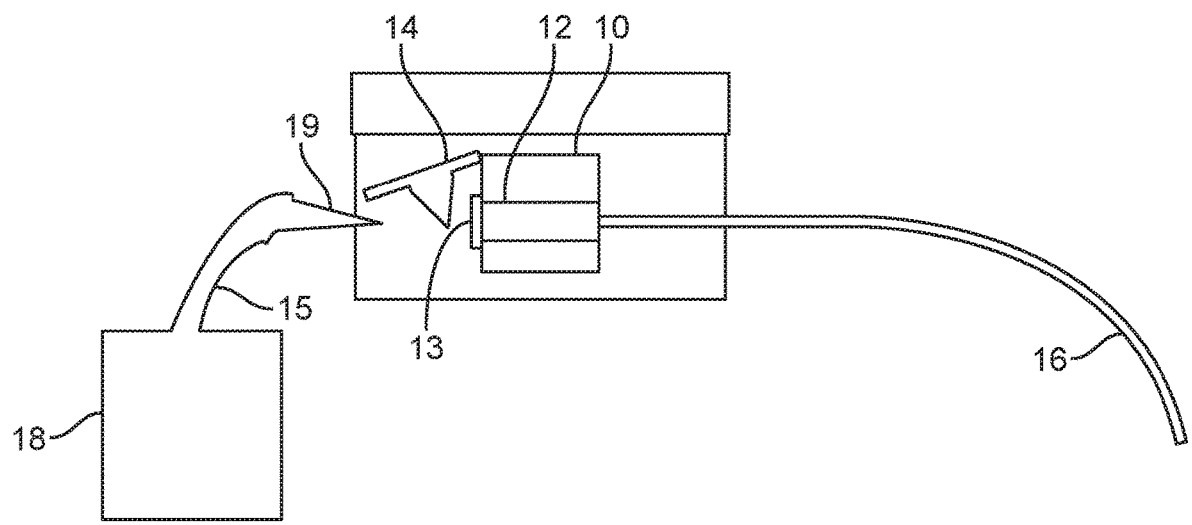
FIG. 1 illustrates a minimally invasive gastrointestinal delivery system, according to an exemplary embodiment.

Referring now to FIG. 1, an exemplary embodiment of the minimally invasive system is depicted comprising anchor 10 configured to be disposed in a mouth of an individual, and channel 12 disposed inside of anchor 10, tube 16, and administration set 18 for supplying a payload to the system. Channel 12 comprises a lumen for receiving tube or track 16. Anchor 10 secures the upstream end of tube 16 inside the mouth of an individual, from where it passes down the lateral oropharynx to the desired site in the gastrointestinal tract. Tube 16 comprises an elongated conduit, and has an upstream end for being secured in the mouth, and a downstream end for placement in a gastrointestinal tract site of the individual. The upstream end includes access port 13. The downstream end includes an exit port (not shown). The exemplary embodiment further comprises cap 14 for removably sealing access port 13 of tube 16. Cap 14 is shown as attached to anchor 10 as shown in FIG. 1. In some other embodiments, the cap may be directly attached to the channel, the access port, or the tube or track. Administration set 18 comprises administration conduit 15 having delivery port 19 at its distal end. Delivery port 19 is configured to engage access port 13 for delivering the payload from administration system 18. The cap preferably is of a size that prevents it being apparent externally, for example, having an external diameter in the range of about 1.0 mm to about 15.0 mm.

In some embodiments, the tube is sealed when not in use by a one-way valve, in addition to, or in lieu of, a cap. In some embodiments, the distal port also includes a one-way valve to prevent reflux of delivered substances up the tube.

In some embodiments, tube 16 of FIG. 1 is replaced with a track, which is an elongated solid line. The track is configured to guide substances or stimulus to a selected site in the gastrointestinal tract. The proximal end of the track is configured to allow the payload to be loaded. The payload may be a substance, a container containing the substance, devices for delivering stimulations, or a monitoring device. The proximal end of the track further comprises attaching the coupler for coupling the track to an anchor or a channel. In some embodiments, for example, the coupler comprises a thickening of the track material, a hook, or a clasp. The coupler preferably is of a size that prevents it being apparent externally, for example, having an external diameter in the range of about 0.1 mm to about 10.0 mm.

In some embodiments, a track is disposed inside or in addition to a tube, allowing therapeutic or diagnostic substances to be guided to a desired site in the gastrointestinal tract.

The tube or track in accordance with the present disclosure may be about 5 cm to 9 meters in length, and preferably has a variety of length for reaching different sites in the gastrointestinal tract, based on the characteristics of an individual patient, and the purpose of the usage. For example, specific lengths of the tube or track may be selected to reach the stomach, upper intestine, mid-intestine, lower intestine, and/or one or more specific sites. The length of the tube or track may also be selected based on the purpose of the use, for example, delivering drugs such as Levodopa to the upper intestine in an individual with Parkinson's disease.

The system is not visible externally between administrations and may be used to administer nutrients, fluid, medications, nutraceuticals, dietary supplements and/or non-nutrient gastrointestinal stimulants or inhibitors, therapies, or monitoring devices directly to a desired site in the gastrointestinal tract in humans and animals.

The Anchor

FIGS. 2A-2G depict some embodiments of anchors configured to secure the channel and the tube or track inside the mouth of an individual. The advantages of securing the tube or track inside the mouth include, among other things: reduced possibility of accidentally or deliberately dislodging; allowing the anchor to remain in place for months or years, even when the tube is being replaced; providing more comfort than standard nasoenteral and oroenteral placement;

being less invasive than percutaneous methods; reduced likelihood of nasal mucosal irritation and damage or sinusitis comparing to nasoenteral tubes; reducing unwanted attention by being invisible when in situ; avoiding the need for taping on the face or other means of securing the tube; minimizing the risk of accidental damage to the tube such as by a razor while shaving; allowing for oral placement of a tube that does not cause or causes minimal gagging; and interference with speech, swallowing or eating.

The anchor may be used to secure the device to a feature in the mouth, such as a bone, cartilage, or a tooth of the individual. The tooth is preferably an upper molar or a premolar. In some embodiments, the feature in the mouth includes muscle or mucosa of the individual. The anchor site may be chosen for comfort and ease of access. For instance, the buccal surface of an upper molar is easy to access and not near the gag reflex mechanism. Such anchoring may be achieved in an outpatient procedure, with no need for anesthesia or special skills, and is easily reversible. Alternatively, the anchor can be fixed to the maxilla or the mandible. In other embodiments the anchor may be secured to fixed or removable dentures, to dental crowns, or to other artificial structures in the mouth, such as a dental prosthesis, or an orthodontic appliance of the individual.

The anchor in accordance with some embodiments of the present disclosure includes a dental prosthesis, an orthodontic appliance inherently suitable for, specifically designed for, or adapted for this purpose, or a specially designed intraoral hardware for attaching the tube or tract, and/or the channel to the selected feature in the mouth. The anchor may be custom made for the purpose of this invention, and usable by many individuals or may be custom made or adjusted for individuals following the design described herein. In some embodiments, the dental prosthesis or orthodontic appliance is modified for the specific purpose of securing the tube, channel, or track, in the mouth. In some other embodiments, commercially available dental prosthesis or orthodontic appliance for dental or orthodontic purposes can be used if inherently suitable for, specifically designed for, or adapted for this purpose.

The anchor may be constructed of one or more materials. For example, the anchor may be constructed of one or more of plastic, composite, ceramic, or metal or engineered biotissue. It may be 3D printed to be of a standard or customized design.

Figure 2A:
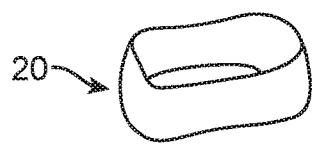
FIGS. 2A-2G illustrate exemplary embodiments of anchors.
Figure 2B:
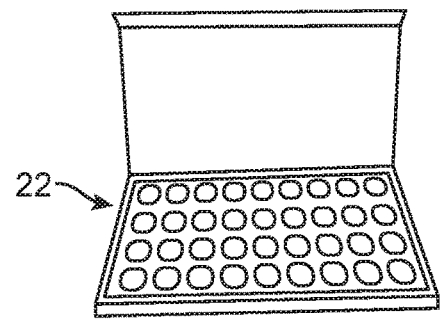

In one embodiment, the anchor is a stainless steel orthodontic molar band 20 with a channel attached thereto, as shown in FIG. 2A. Molar bands are available in several different sizes and shapes to provide a secure fit around a tooth, as shown in FIG. 2B, and is configured to be cemented in place with dental cement. Molar band 20 may be attached to an upper or lower molar, and/or a first, second or third molar. Molar band 20 may also be attached to a premolar. One or more primary (deciduous) or secondary (permanent) teeth may be used to anchor the tube or track. In some embodiments, the channel is disposed at the buccal surface of molar band 20.

Figure 2C:
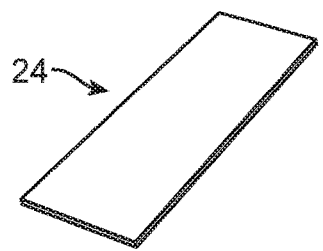

In one embodiment, the anchor comprises a flat stainless steel or other biocompatible strip, as shown in FIG. 2C, which may be bonded onto the buccal aspect of one or more adjacent molars. In another embodiment, the anchor comprises a metal or other biocompatible strip secured, e.g., with screws to a bone in the mouth. An example of the strip is orthodontic "miniplates" as made by Tita-Link. Similarly "bollard" type anchors may be used as made by Tita-Link. See: http://www.tita-link.com.

Figure 2D:
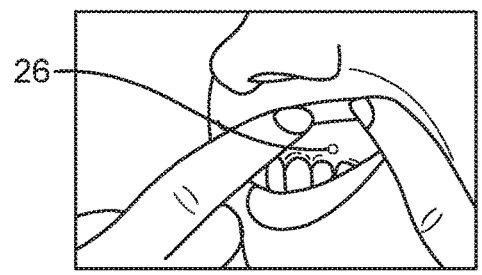

Referring now to FIG. 2D, in some embodiments, the anchor comprises an orthodontic temporary anchoring device ("TAD") 26. In some embodiments, TAD 26 is attached to a channel. In some other embodiments, TAD 26 can be modified to include a channel that allows passage of the tube or track therethrough. The modified or unmodified TAD may be placed in the maxilla or mandible through the gingival oral mucosa at a site that allows the tube or track to be secured inside the mouth and pass easily into the lateral oropharynx. This embodiment may be used in edentulous individuals including infants and the elderly, and individuals who do not have a suitable tooth, or for any other reasons or considerations. Such anchor sites may be of particular value in individuals without suitable teeth of their own that can otherwise serve to secure the anchors.

In one embodiment, the anchor comprises a dental implant secured into an empty tooth socket 28. Such an anchor may also be of particular value in individuals without suitable teeth of their own that can otherwise serve as anchors.

In some embodiments, the anchor is clipped over or otherwise secured on one or more natural or artificial teeth in a manner that is functional, safe and comfortable. In one such embodiment, the anchor comprises a dedicated dental plate, for example, a clip on dental plate 31 (e.g., similar to a retainer) placed specifically to serve as an anchor, as shown in FIG. 2G. In some other embodiments, the anchor includes a denture, dental braces, a dental bracket, or a dental retainer.

Figure 2E:
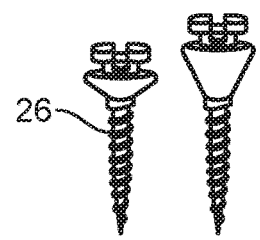
Figure 2E:
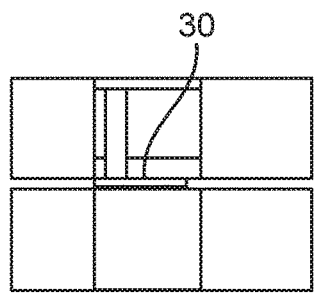
Figure 2F:
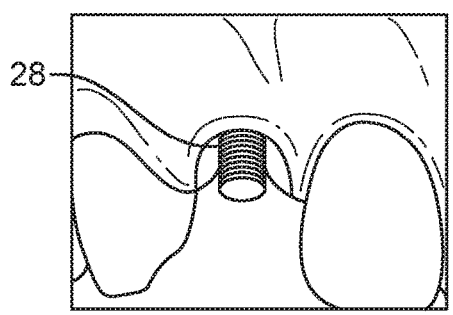
Figure 2G:
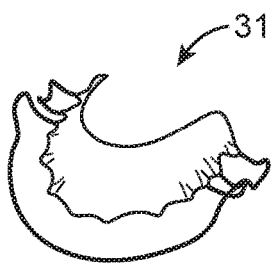

Referring now to FIG. 2E, an anchor in accordance with the present disclosure may further comprise bite block 30 that fits between the occlusal surfaces of the teeth to prevent inadvertent or deliberate biting on the tube or track. In some other embodiments, a bite block is disposed at the proximal end of the tube or track.

The Channel

Figure 3A:
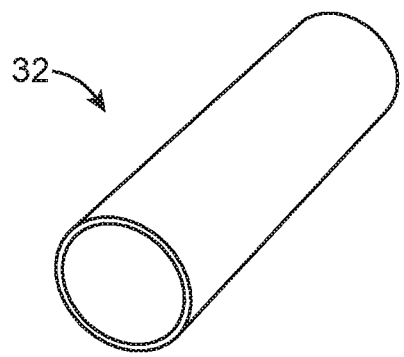
FIGS. 3A-3C illustrate exemplary embodiments of channels.
Figure 3B:
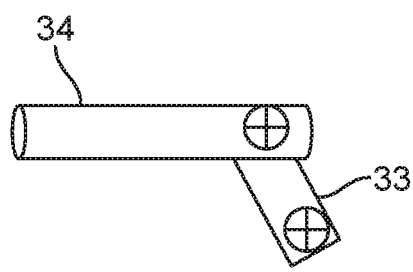
Figure 3C:
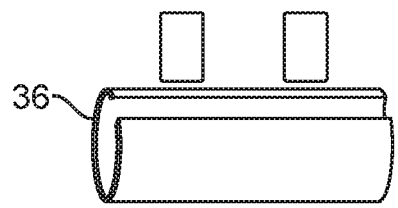

The channel prevents the tube or track from migrating distally down the intestinal tract. It helps direct the tube or track away from the occlusal surface of the teeth. It helps direct the tube or track down the lateral oropharynx, away from the sensitive posterior palate and medial pharynx. In one aspect, the channel is narrow enough that the proximal end of the tube or track and access port cannot pass through. In another aspect, the channel is wide enough such that the main body of the tube or track passes through with little or no resistance. The channel is available in several different sizes to accommodate a chosen tube diameter. In one aspect, the channel is small so as to minimize bulk in the mouth both for comfort and for aesthetic reasons (e.g., so that it is not visible as a bulge from the outside). The channel may be attached directly or indirectly to the anchor. Referring now to FIGS. 3A-3C, in one embodiment, channel 32 is a cylinder of stainless steel and welded to an anchor, for example, a molar band, a dental plate, or other intraoral hardware, stainless steel dental or orthodontic appliances of the individual. In one embodiment, the channel is attached indirectly to the anchor in a manner that allows its position to be adjusted in the mouth. For example, channel 34 as shown in FIG. 3B is connected to an anchor by an adjustable connector 33. In another embodiment, the channel is clipped or otherwise secured to the anchor. In one embodiment, the channel comprises a cylinder with a slit opening, through which the tube or track is slotted into the channel. In another embodiment, the channel comprises two hingedly connected semi-cylindrical parts configured to form a lumen when the hinge is closed. The semi-cylindrical parts may be opened to receive the tube or track, which may be securely disposed within the channel when the semi-cylindrical parts are closed.

The channel may be made of any suitable medical grade material. In one embodiment, the channel can be formed of a deformable material (e.g., a plastic or rubber material selected to include a degree of flexibility and shape memory or bioengineered tissue), and can include a longitudinal recess, gap or slit along the channel. As such, the channel can conform to accommodate a passage of the tube or track as it is inserted or pressed through the recess, gap or slit, and then secure the tube or track therein.

The Cap

The cap is configured to seal the tube when the tube is not in use. This prevents food particles or other matter from entering the tube and also prevents reflux of intestinal secretions and other intestinal substances regurgitating into the mouth. The cap may also serve to hold the tube in the channel rather than spontaneously pushing forward out of the mouth. The cap preferably is small to minimize bulk in the mouth both for comfort and for aesthetic reasons (e.g., so that it is not visible as a bulge from the outside), and has an external diameter and depth in the range of about 1 mm to about 10.0 mm, and has a depth in the range of about 1.0 mm to about 10.0 mm. In some embodiments, the cap comprises a first surface engageable with the tube, and a second surface substantially opposite to the first surface. The first surface may have a cross sectional diameter in the range of about 5.0 mm to about 12.0 mm. The second surface may have a cross sectional diameter in the range of about 0.1 mm to 5.0 mm. The length of the cap as measured from the first and second surfaces is about 1.0 mm to 10.0 mm. The cap is available in several different sizes to accommodate a chosen tube internal diameter and can be comprised of metal, plastic or other biocompatible material.

Figure 4A:
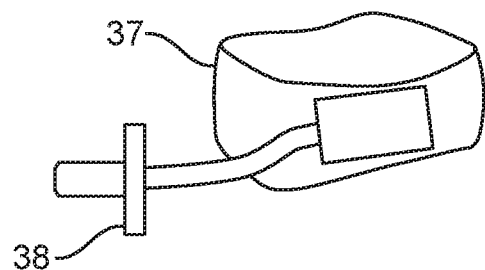
FIGS. 4A-4C illustrate exemplary embodiments of sealing mechanisms.
Figure 4B:
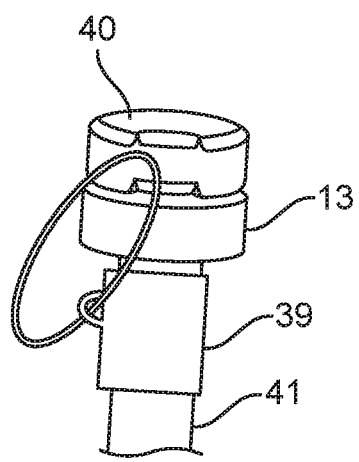
Figure 4C:
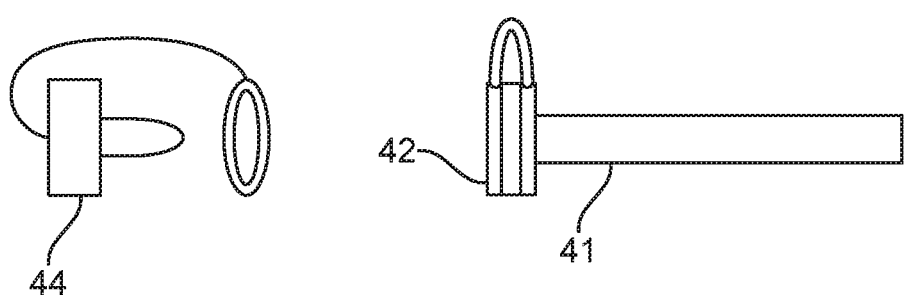

Referring now to FIGS. 4A-4C, various arrangements of the cap may be used in accordance with the present disclosure. For example, in one embodiment, cap 38 is tethered or otherwise engaged to anchor 37, as shown in FIG. 4A. In another embodiment, cap 40 is tethered to channel 39, as shown in FIG. 4B. In yet another embodiment, cap 42 is tethered or otherwise engaged to tube 41. In yet another embodiment, cap 44 is a separate component from the tube, the anchor, or the channel.

The Tube or Conduit

As seen in FIG. 5A, the tube or conduit in accordance with the present disclosure comprises a medical grade feeding tube with a small access port.

The tube may be small (e.g., 5-12 French) or large (e.g., 14-24 French) bore diameter and of different lengths, thereby allowing delivery of substances of different consistencies (e.g., water, crushed pills, soft diet) to different gastrointestinal sites (e.g., stomach, jejunum, or ileum). In some embodiments, the tube is 8 French, 9 French, or 10 French. Table 1 below shows a conversion chart of the French scale to millimeters.

TABLE 1

| French Size | Inner Diameter | Outer Diameter |
|---|---|---|
| 5 | 0.043 (in) | 0.065 (in) |
| | 1.09 (mm) | 1.65 (mm) |
| 6 | 0.054 (in) | 0.086 (in) |
| | 1.37 (mm) | 2.18 (mm) |
| 8 | 0.077 (in) | 0.113 (in) |
| | 1.96 (mm) | 2.87 (mm) |

TABLE 1-continued

| French Size | Inner Diameter | Outer Diameter |
|---|---|---|
| 10 | 0.1 (in) | 0.14 (in) |
| | 2.54 (mm) | 3.56 (mm) |
| 12 | 0.105 (in) | 0.16 (in) |
| | 2.67 (mm) | 4.06 (mm) |

The access port allows substances to be delivered down the tube, and yet is small to minimize bulk in the mouth both for comfort and for aesthetic reasons (e.g., so that it is not visible as a bulge from the outside). As seen in FIG. 5A, access port 46 has an internal diameter slightly larger than that of tube 45 (e.g., about 0.2 mm to about 3.0 mm larger in external diameter than that of the tube).

In some embodiments, the access port includes female thread 52 configured to allow connection to a compatible male thread 53 of an administration set.

In another embodiment, as shown in FIG. 5E, access port 54 may comprise one-way valve to allow access by a compatible administration set.

The tube may comprise one or more segments, and any one segment may be a solid or flexible construction, and may be made from one or more materials such as plastic, composite, ceramic, polymer, biodegradable material, bioscaffolding or metal. One or more materials used may be suitable for minimizing twisting and kinking and to direct the tube via a preferred route through the oropharynx.

In some embodiments, tube 46 is reinforced 48 at its upstream end to prevent it from being inadvertently perforated through deliberate or inadvertent biting, as seen in FIG. 5B. The tube may be reinforced using methods known in the art, such as using a metallic material or a resilient polymeric material with various physical and structural conformations, such as a web or spiral configuration.

In some embodiments, the tube is long enough to reach the selected site in the gastrointestinal tract, for example, the stomach, the duodenum, the jejunum or the ileum, from the mouth. The tube may be contoured to the shape of an oral and pharyngeal anatomy of an individual to prevent occlusion of the tube. Contouring can also enhance comfort by preventing the tube from irritating soft tissue during prolonged wear. Contouring of the tube can be achieved using shape memory wires that have been "shape set" to adapt to a specific anatomy of an individual, allowing for optimal passage through the oropharynx by angling away from the occlusal surface of the teeth and the sensitive medial palate and oropharynx, as seen in FIG. 5C. Shape memory wires may also function as a device that counteracts the peristalsis response of a body to prevent a tube from undergoing prolonged tensile forces.

In some embodiments, the tube may be retrievable from the gastrointestinal tract of an individual. For example, the tube may be withdrawn from the gastrointestinal tract and removed from a channel anchored to a tooth of an individual. A replacement tube (e.g., swapped onto an access port, or including a new access port altogether) may then be inserted into the channel, and subsequently disposed in the gastrointestinal tract of the individual. In some embodiments, the tube may be partially withdrawn for inspection, e.g., for damage or wear and tear.

In some embodiments, the shape contours of a tube can be determined from 3D imaging scans of the anatomy of an individual. Alternatively, a tube can take the form of a generic contour predetermined by a manufacturer or a doctor.

In some embodiments, the tube comprises a decoupler dividing the tube into an upstream segment and a downstream segment. When deployed in the body of an individual, the downstream segment may be disposed in the gastrointestinal tract of the individual. As such, if the downstream segment is no longer needed or needs to be replaced, the decoupler can disengage the downstream segment from the upstream segment. For example, the decoupler may be configured to disengage in response to an electrical stimulus (e.g., an electrical signal, which may, for example, be transmitted across an electrical wire from an access port) or a mechanical force (e.g., a pull tab or cord associated with the decoupler). Upon disengaging from the upstream segment, the downstream segment may pass through the remainder of the gastrointestinal tract. In some arrangements, the downstream segment is broken down and absorbed in the gastrointestinal tract (e.g., is formed of catgut, polyglycolic acid, polylactic acid, polydioxanone, caprolactone, and other similar natural or synthetic dissolvable materials). Further, in some arrangements, multiple decouplers can divide the tube into corresponding multiple segments.

The access port allows substances to be delivered down the tube, and yet is small to minimize bulk in the mouth both for comfort and for aesthetic reasons (e.g., so that it is not visible as a bulge from the outside). The access port may have a screw thread 53 to allow connection to a compatible administration set. The access port may comprise one-way valve 54 to allow access by a compatible administration set.

In some embodiments, the tube includes an expandable distal reservoir at its downstream end, which may be filled or emptied as desired with a depot supply of a substance including nutrients or medication that can be released from the distal reservoir. The distal reservoir preferably releases the substance in a controlled manner through mechanisms such as a semipermeable membrane to provide a local delivery of substance for a sustained period. This distal reservoir may be of varying lengths and expand to varying diameters to achieve therapeutic goals. A relatively large diameter may exert a local pressure effect, while a smaller diameter may not exert any local pressure effect. The tube can be used, for example, to fill and empty an intragastric or intraintestinal balloon sealingly engaged at the downstream end with air or liquid, for achieving varying amounts of pressure in the balloon. In some embodiments, the tube can be used with a pump to drain gastric secretions, gas, gastric acid, or nutrients from the gastrointestinal tract.

Administration System

Figure 6A:
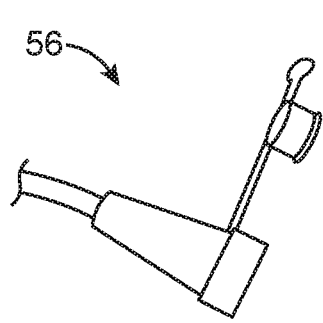
FIGS. 6A-6F illustrate exemplary embodiments of administration sets.
Figure 6B:
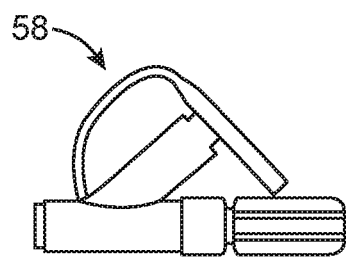
Figure 6C:
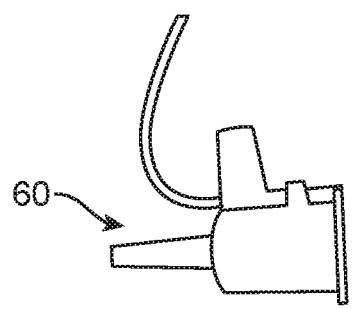
Figure 6D:
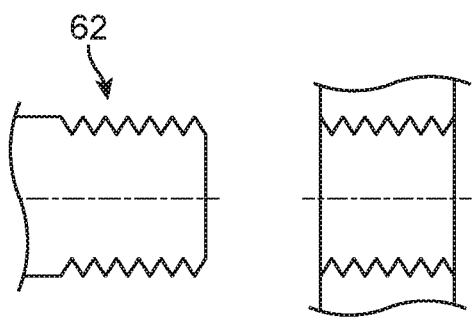

The administration system is configured to deliver substances to the tube securely through the access port. The administration system may include one channel as seen in FIG. 6A, or more than one channel, such as the dual channel administration system as seen in FIG. 6B, to allow simultaneous passage of more than one item (e.g., air and a stylet). The administration system will also allow for connection of the tube to a standard delivery system, e.g., a catheter tip connector 60 or a Luer lock adapter.

Figure 6E:
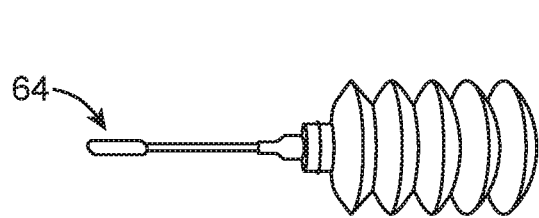
Figure 6F:
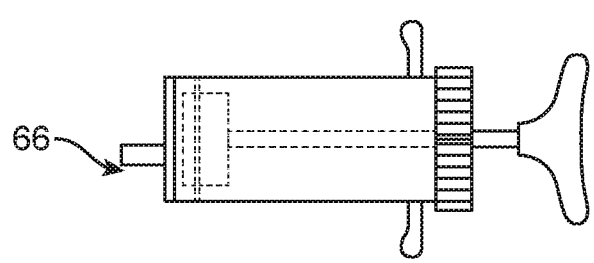

The administration system can further comprise a payload such as tube feed or other material for administration via the tube in a pre-filled container or reservoir that can connect directly to the access port. The reservoir may then be squeezed, as seen in FIG. 6E or pushed by a plunger distally down the tube, as seen in FIG. 6F.

In one aspect, the access port is not configured as plain tapered needles or Luer lock devices. In another aspect, the access port is configured to be fastened to a pre-selected feature that is unique or specific to the access port, thereby preventing misadministration.

In some embodiments, the administration system is configured to deliver substances or devices by loading the substances or devices onto the track, as described in more detail below.

The advantages of the present invention compared with the prior art include:

The system is not externally visible between administrations.

It is less easy to dislodge accidentally or deliberately than prior art enteral feeding systems.

It is more comfortable than prior art nasoenteral systems.

It is less invasive than percutaneous methods.

It is less likely to cause nasal mucosal irritation and damage or sinusitis than nasoenteral tubes.

It is not visible when in situ thereby reducing unwanted attention.

It avoids the need for taping on the face or other means of securing the tube.

It minimizes the risk of accidental damage to the tube such as by a razor while shaving.

It allows for oral placement of a tube that causes little or no gagging, or interference with speech, swallowing or eating or other typical daily activities.

It is positioned in a way that avoids or minimizes biting on the tube.

It is a reversible system: all components may be removed and/or replaced. The tube or track may be withdrawn through the mouth. Slow release delivered materials such as depot medications may be withdrawn prior to full release if so desired.

Certain components may be released (e.g., empty medication pods, docking bumpers) to progress distally down the gastrointestinal tract or may be designed to be biodegraded at a desired time and place, including the administration track itself, somewhat analogous to dissolving sutures.

The tube is preferably not compatible with standard small bore medical connectors, thereby preventing misadministration of an enteral feeding or medication by the wrong route. In addition, the access port for the platform is also preferably not compatible with generic or currently available access systems such as plain tapered needles or Luer lock devices.

The present invention may also be used for novel applications including discreet and sustainable:

Administration of medication at a desired rate and location in the gastrointestinal tract;

Mechanical distension;

Electrical stimulus;

Chemical stimulus;

Nutritional stimulus to regulate gastrointestinal motility and/or neurohormonal signaling;

Monitoring of gastrointestinal processes;

Chemotherapy, radiotherapy, immunotherapy, and anti-inflammatory therapy.

Depot therapeutic or prophylactic agent release;

Delayed release of therapeutic or prophylactic agent.

Exemplary Conduit Embodiments

Figure 7:
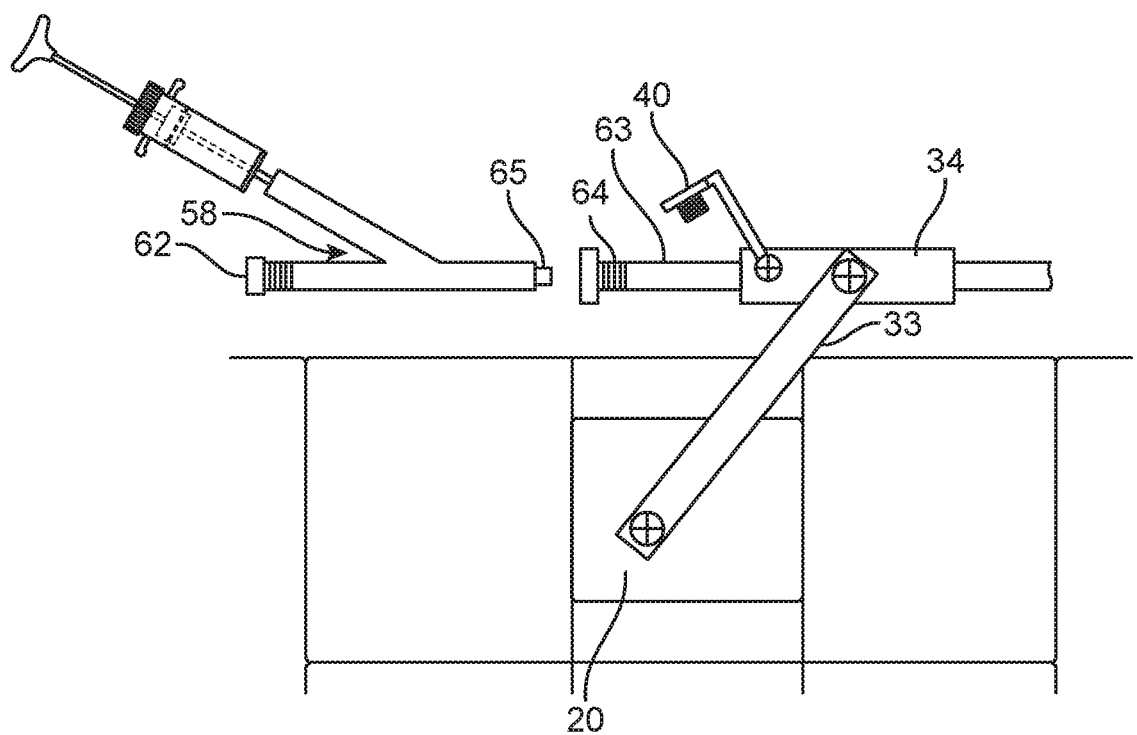
FIG. 7 illustrates a minimally invasive gastrointestinal delivery system, according to another exemplary embodiment.

Referring now to FIG. 7, an embodiment includes: stainless steel molar band 20, stainless steel channel 34 with adjustable connector 33 to position the channel at an optimal location; and stainless steel cap 40, which is integrated into channel 34 to maintain tube 63 in position and seal it when not in use. Tube 63 comprises screw thread 64 for connection to dual lumen access adapter 58 having a compatible screw thread 65. The proximal end 62 of access adapter 58 may be compatible with Luer lock syringes. In some other embodiments, access adapter 58 is configured to be not compatible with generic or currently available access systems such as plain tapered needles or Luer lock devices, and is only compatible with a specifically designed administration system to avoid misadministration. In some embodiments, stainless steel cap 40 is replaced with a one-way valve.

Figure 8:
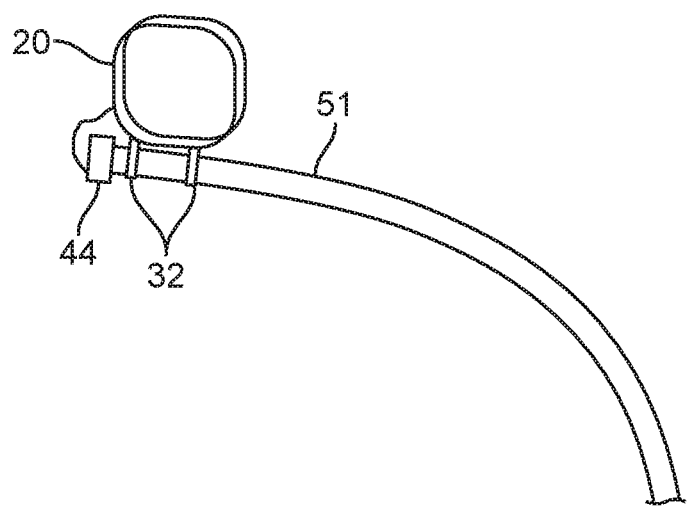
FIG. 8 illustrates a minimally invasive gastrointestinal delivery system, according to yet another exemplary embodiment.

Referring now to FIG. 8, an alternative embodiment includes: stainless steel molar band 20 situated on an upper first molar; stainless steel channel 32 comprising two rings attached to molar band 20 on the buccal aspect anterior to bulk of the masseter muscle; and stainless steel cap 44 is sealingly engageable with tube 52 to seal it when not in use. Stainless steel cap 44 has an outer diameter larger than the diameter of the rings of stainless steel channel 32, thereby maintaining the upstream end of tube 51 in channel 32. Stainless steel cap 44 is coupled to molar band 20 via a suture or a wire. In an alternative embodiment, cap 44 is replaced with a one-way valve.

Exemplary Track Embodiments

Figure 9A:
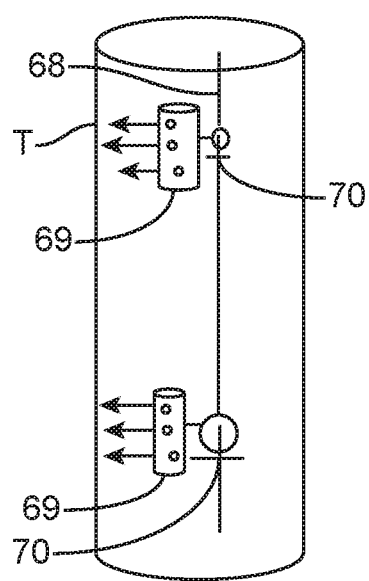
FIGS. 9A-9D illustrate exemplary embodiments having an elongated track.
Figure 9B:
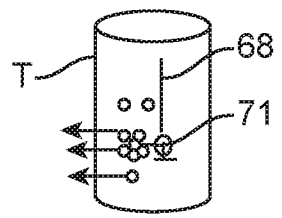
Figure 9C:
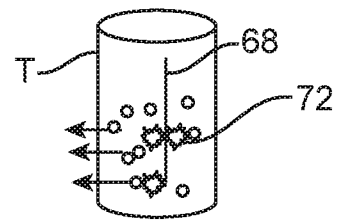

Referring now to FIGS. 9A-9D, embodiments in accordance with the present disclosure comprise track 68 having its downstream end disposed in gastrointestinal tract T. Track 68 preferably comprises bumper 70 for stopping administered substances at a desired point in the gastrointestinal tract for controlled release. In some embodiments, bumper 70 is configured to stop the substance containers or devices at a selected gastrointestinal tract site. Track 68 is configured to be secured within a channel, which is attached to an anchor in the mouth. Substances for delivery to a specific point in the gastrointestinal tract may be contained in a dosage pod, e.g., a large reservoir at a stomach or further down the gastrointestinal tract, which may be loaded at the upstream end of the track. For example, substances or the dosage pod(s) may be clipped loosely around the track near the anchor and then swallowed by the individual. Alternatively, the substances or the dosage pod(s) may be slid or threaded over the track. As seen in FIG. 9A, two dosage pods 69 containing the substances to be administered are slid down the track, the location of each on the track is fixed by bumper 70. In some embodiments, each dosage pod comprises a plurality of distribution ports, which may be selectively permeable. Multiple dosage pods comprising different types of substances may be delivered to a selected site or sites of the gastrointestinal tract.

In some embodiments, the track is temporarily disconnected from the anchor before loading.

Administered substances may be in a solid form, a liquid form, or a semi-liquid form, and may include, but are not limited to, nutritional or nutraceutical stimuli for regulating gastrointestinal motility, and/or neurohormonal signaling including appetite and glucose levels, medication and chemical stimuli. Several doses of medication may be administered at one time and maintained in a dosage pod and released in a controlled manner. This may be used to improve adherence to medication use where repeated doses are important (e.g., antibiotics, chemotherapy, oral contraceptives, HIV, tuberculosis, thyroid medication, etc.). Currently, orally ingested materials generally pass distally along the gastrointestinal tract necessitating repeat dosing. This leads to suboptimal medical management when the required doses are not taken in the correct amount or at the right time.

Figure 9D:
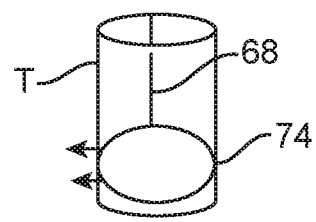

In some embodiments, the track is configured to deliver one or more devices providing chemical, electrical or mechanical stimulations to a selected site or sites of the gastrointestinal tract. For example, a substance can be delivered through the track for providing chemical stimulation 71 to a selected site of the gastrointestinal tract T. For another example, electrodes can be delivered down the track for providing electrical stimulation 72. Balloon 74 may be delivered down the track, which can be intermittently inflated and deflated to provide mechanical stimulation to the gastrointestinal tract, as seen in FIG. 9D. In some embodiments, the track is used to deliver a radiofrequency device or an ultrasonic device to a selected site of the gastrointestinal tract. In some embodiments, the track delivers a monitoring device to a selected site of the gastrointestinal tract. For example, a pH sensor can be maintained in the esophagus to monitor for acid reflux, a camera or other means of detecting occult bleeding (e.g., a Guaiac-based system) may be placed near an ulcer to monitor for increased risk of or actual bleeding.

It is to be understood that, while the invention has been described in conjunction with the above embodiments, the foregoing description and examples are intended to illustrate and not limit the scope of the invention. Other aspects, advantages and modifications within the scope of the invention will be apparent to those skilled in the art to which the invention pertains.

What is claimed is:

1. A gastrointestinal administration device comprising:
an elongated conduit having an upstream end configured to be disposed in a mouth of an individual, a downstream end configured to be disposed in a gastrointestinal tract site of the individual, a wall defining a lumen, the lumen extending therethrough the upstream end and the downstream end, an access port in fluid communication with the upstream end, and at least one distribution port in fluid communication with the downstream end;
a sealing mechanism for sealing the access port;
an anchor configured to be disposed in the mouth, the anchor configured to secure the upstream end of the elongated conduit to at least one feature in the mouth; and
a channel coupled to the anchor via an adjustable connector that has a first end and a second end,
wherein the adjustable connector is configured to be attached to the anchor at the first end and to the channel at the second end such that the channel is spaced apart from the anchor, the second end configured to be displaced relative to the anchor to allow positioning of the channel at a desirable location within the mouth, the channel configured to receive the upstream end of the elongated conduit,
wherein the elongated conduit is translatable through the channel; and
wherein the access port is disposed outside of the channel and is not translatable through the channel.

2. The gastrointestinal administration device of claim 1, wherein the channel comprises a longitudinal recess along an entire length of an inner surface of the channel, the longitudinal recess configured to slidably receive the elongated conduit.

3. The gastrointestinal administration device of claim 1, further comprising at least one of a sensor, an expandable distal reservoir, and a pump disposed at the downstream end of the elongated conduit.

4. The gastrointestinal administration device of claim 1, wherein the elongated conduit comprises an upper segment and a lower segment, the lower segment is formed of a biodegradable material configured to be absorbable in a gastrointestinal tract of the individual.

5. The gastrointestinal administration device of claim 1, further comprising an administration conduit having a proximal end and a distal end, the administration conduit in fluidic communication with a delivery port at the distal end and a first reservoir including a payload at the proximal end,
wherein the delivery port is removably engageable to the access port of the elongated conduit; and
wherein upon an engagement of the delivery port to the access port, a pressure at the first reservoir provides the payload through the at least one distribution port and into the gastrointestinal tract site.

6. A method for minimally invasively accessing a selected gastrointestinal tract site of an individual, the method comprising:
selecting an elongated conduit having an upstream end and a downstream end, a lumen extending therethrough, an access port in fluid communication with the upstream end, and at least one distribution port in fluid communication with the downstream end;
selecting an anchor and a channel for placement in the mouth;
coupling the channel to the anchor via an adjustable connector that has a first end and a second end;
inserting the downstream end of the elongated conduit into the channel, such that the access port is disposed outside of the channel and is not translatable through the channel;
placing the downstream end in the selected gastrointestinal tract site; and
placing the upstream end in a mouth of the individual,
wherein the anchor is attached to at least one feature in the mouth, and
wherein the adjustable connector is configured to be attached to the anchor at the first end and to the channel at the second end such that the channel is spaced apart from the anchor, the second end configured to be displaced relative to the anchor to allow positioning of the channel at a desirable location within the mouth.

7. The method of claim 6, further comprising:
selecting an administration conduit having a proximal end and a distal end, the administration conduit in fluidic communication with a delivery port at the distal end and a first reservoir including a payload at the proximal end; and
delivering the payload to the elongated conduit through the at least one distribution port to the gastrointestinal tract.

8. The method of claim 6, further comprising:
sealingly engaging the downstream end of the elongated conduit with an intragastric or intraintestinal balloon, the intragastric or intraintestinal balloon configured to be disposed in the vicinity of the selected gastrointestinal tract site;
inflating the intragastric or intraintestinal balloon by delivering a second substance through the elongated conduit into the intragastric or intraintestinal balloon; and
optionally deflating the intragastric or intraintestinal balloon.

9. The method of claim 6, further comprising pumping a third substance from the selected gastrointestinal tract site to the upstream end of the elongated conduit.

10. A gastrointestinal administration device comprising:
an elongated track having an upstream end configured to be disposed in a mouth of an individual, a downstream end configured to be disposed in a gastrointestinal tract site of the individual, and a coupler disposed at the upstream end of the elongated track, the elongated track configured to deliver a substance or a device to a selected site of the gastrointestinal tract;
an anchor configured to be disposed in the mouth, the anchor configured to secure the upstream end of the elongated track to at least one feature in the mouth; and
a channel coupled to the anchor via an adjustable connector that has a first end and a second end,
wherein the adjustable connector is configured to be attached to the anchor at the first end and to the channel at the second end such that the channel is spaced apart from the anchor, the second end configured to be displaced relative to the anchor to allow positioning of the channel at a desirable location within the mouth, the channel configured to receive the upstream end of the elongated track,
wherein the coupler is coupled to the channel.

11. The gastrointestinal administration device of claim 10, further comprising at least one sensor disposed at the downstream end of the elongated track, the at least one sensor configured to sense at least one of pH and blood at a vicinity of the selected site of the gastrointestinal tract.

12. The gastrointestinal administration device of claim 10, wherein the elongated track comprises an upper segment and a lower segment, the lower segment is formed of a biodegradable material absorbable in a gastrointestinal tract.

13. The gastrointestinal administration device of claim 12, wherein the elongated track further comprises a decoupler configured to selectively engage the upper segment and the lower segment.

14. The gastrointestinal administration device of claim 10, wherein the device comprises a stimulation device configured to provide one or more stimulus to the vicinity of the selected site of the gastrointestinal tract, the stimulus comprising electrical, chemical, or mechanical stimulus.

15. A method for minimally invasively delivery of a substance or a device to a selected site of the gastrointestinal tract of an individual, the method comprising:
selecting an elongated track having an upstream end and a downstream end;
selecting an anchor and a channel for placement in the mouth;
coupling the channel to the anchor via an adjustable connector that has a first end and a second end;
inserting the elongated track through the channel;
coupling the upstream end of the elongated track to the channel;
placing the downstream end of the elongated track in the selected site of the gastrointestinal tract;
placing the upstream end of the elongated track in a mouth of the individual; and
delivering the substance or device to the selected site of the gastrointestinal tract by coupling the substance or device to the elongated track,
wherein the adjustable connector is configured to be attached to the anchor at the first end and to the channel at the second end such that the channel is spaced apart from the anchor, the second end configured to be displaced relative to the anchor to allow positioning of the channel at a desirable location within the mouth, the anchor configured to be attached to at least one feature in the mouth.

16. The method of claim 15, wherein delivering the device to the selected site of the gastrointestinal tract comprises delivering a stimulation device configured to provide at least one of an electrical, chemical, or mechanical stimulus to the selected site of the gastrointestinal tract.

17. The method of claim 15, wherein selecting an elongated track further comprises selecting an elongated track having a bumper disposed at the downstream end thereof, the bumper configured to selectively obstruct the substance or device from moving further downstream relative to the elongated track.

* * * * *